United States Patent [19]

Staples et al.

[11] Patent Number: 5,000,940

[45] Date of Patent: Mar. 19, 1991

[54] DEVICES, COMPOSITIONS AND THE LIKE HAVING OR CONTAINING AN INORGANIC PYROPHOSPHATE

[75] Inventors: Lorna C. Staples, Teaneck; Henry C. Spanier, West Milford; Felice Scaglione, Hasbrouck Heights; Jan Karwowski, Franklin Lakes, all of N.J.

[73] Assignee: Nabisco Brands, Inc., East Hanover, N.J.

[21] Appl. No.: 358,163

[22] Filed: May 30, 1989

[51] Int. Cl.$^5$ .................... A23K 1/18; A23K 7/20
[52] U.S. Cl. ................................. 424/49; 424/53; 424/57; 424/442; 426/549; 426/551; 426/805
[58] Field of Search ............... 424/442, 49, 53, 57; 426/89, 94, 302, 289, 549, 551, 560, 805

[56] References Cited

U.S. PATENT DOCUMENTS

| | | | |
|---|---|---|---|
| 3,488,419 | 1/1970 | McCune et al. | 424/49 |
| 3,535,420 | 10/1970 | McCune et al. | 424/49 |
| 3,567,459 | 3/1971 | Wruk, III et al. | 99/2 |
| 3,639,569 | 2/1972 | Medcalf, Jr. | 424/48 |
| 3,686,393 | 8/1972 | Woodruff et al. | 424/50 |
| 3,701,830 | 10/1972 | Welwrich et al. | 424/94 |
| 3,871,334 | 3/1975 | Axelrod | 119/29.5 |
| 3,882,257 | 5/1975 | Cagle | 426/274 |
| 3,899,607 | 8/1975 | Miller et al. | 426/285 |
| 3,934,002 | 1/1976 | Haefele | 424/54 |
| 3,942,537 | 3/1976 | Evers et al. | 131/278 |
| 3,956,479 | 5/1976 | Bauman | 424/54 |
| 3,957,964 | 5/1976 | Grimm, III | 424/10 |
| 3,959,458 | 5/1976 | Agricola et al. | 424/52 |
| 4,003,971 | 1/1977 | Mannara | 264/9 |
| 4,044,158 | 8/1977 | Burkwall, Jr. | 426/271 |
| 4,145,447 | 3/1979 | Fisher et al. | 426/72 |
| 4,153,732 | 5/1979 | Muhler et al. | 426/72 |
| 4,215,149 | 7/1980 | Majlinger | 426/292 |
| 4,254,101 | 3/1981 | Demny, Jr. | 424/52 |
| 4,259,358 | 3/1981 | Duthie | 426/46 |
| 4,260,635 | 4/1981 | Fisher | 426/3 |
| 4,314,990 | 2/1982 | Denny, Jr. et al. | 424/52 |
| 4,323,551 | 4/1982 | Parran, Jr. | 424/54 |
| 4,364,925 | 12/1982 | Fisher | 424/50 |
| 4,419,372 | 12/1983 | Greene et al. | 426/635 |
| 4,421,527 | 12/1983 | Wason | 51/308 |
| 4,472,373 | 9/1984 | Ryan | 424/54 |
| 4,513,014 | 4/1985 | Edwards | 426/132 |
| 4,515,770 | 5/1985 | Besic | 424/49 |
| 4,515,772 | 5/1985 | Parran, Jr. et al. | 424/57 |
| 4,532,124 | 7/1985 | Pearce | 424/52 |
| 4,535,725 | 8/1985 | Fisher | 119/29 |
| 4,540,584 | 9/1985 | Someya | 424/156 |
| 4,557,219 | 12/1985 | Edwards | 119/29.5 |
| 4,627,977 | 12/1986 | Gaffar et al. | 424/52 |
| 4,634,448 | 1/1987 | Ajioka et al. | 8/436 |
| 4,674,444 | 6/1987 | Axelrod | 119/29.5 |
| 4,678,662 | 7/1987 | Chan | 424/57 |
| 4,684,518 | 8/1977 | Parran, Jr. et al. | 424/52 |
| 4,702,929 | 10/1987 | Lehn et al. | 426/635 |
| 4,702,929 | 10/1987 | Lehn et al. | 426/635 |
| 4,735,808 | 4/1988 | Scaglione et al. | 426/62 |
| 4,771,733 | 9/1988 | Axelrod | 119/29.5 |
| 4,771,773 | 9/1988 | Axelrod | 128/341 |
| 4,795,655 | 1/1989 | Spiel et al. | 426/635 |
| 4,802,444 | 2/1989 | Markham et al. | 119/29 |
| 4,806,340 | 2/1989 | Gaffar et al. | 424/52 |
| 4,822,626 | 4/1989 | Spanier et al. | 426/94 |

FOREIGN PATENT DOCUMENTS

| | | |
|---|---|---|
| 168071 | 12/1956 | Australia . |
| 1233121 | 2/1988 | Canada . |
| 079611 | 5/1983 | European Pat. Off. . |
| 0097476 | 1/1984 | European Pat. Off. . |
| 236920 | 3/1987 | European Pat. Off. . |
| 0236290 | 9/1987 | European Pat. Off. . |
| 0236827 | 9/1987 | European Pat. Off. . |
| 2188548 | 10/1987 | European Pat. Off. . |
| 0249398 | 12/1987 | European Pat. Off. . |
| 0251591 | 1/1988 | European Pat. Off. . |
| 0254452 | 1/1988 | European Pat. Off. . |
| 0288909 | 11/1988 | European Pat. Off. . |
| 0291747 | 11/1988 | European Pat. Off. . |
| 0295116 | 12/1988 | European Pat. Off. . |
| 0297211 | 1/1989 | European Pat. Off. . |
| 0297212 | 1/1989 | European Pat. Off. . |
| 0297213 | 1/1989 | European Pat. Off. . |
| 305283 | 3/1989 | European Pat. Off. . |
| 0309414 | 3/1989 | European Pat. Off. . |
| 0311412 | 4/1989 | European Pat. Off. . |
| 0316079 | 5/1989 | European Pat. Off. . |
| 0319516 | 6/1989 | European Pat. Off. . |
| 330075 | 8/1989 | European Pat. Off. . |
| 2643991 | 3/1978 | Fed. Rep. of Germany . |
| 2749581 | 5/1978 | Fed. Rep. of Germany . |
| 3041237 | 6/1982 | Fed. Rep. of Germany . |
| 3426203 | 7/1984 | Fed. Rep. of Germany . |
| 3417235 | 6/1985 | Fed. Rep. of Germany . |
| 3607480 | 9/1987 | Fed. Rep. of Germany . |
| 86/03674 | 7/1986 | PCT Int'l Appl. . |
| 777556 | 6/1957 | United Kingdom . |
| 1179343 | 1/1970 | United Kingdom . |
| 1386627 | 3/1973 | United Kingdom . |
| 2092000 | 8/1982 | United Kingdom . |
| 2109086 | 6/1983 | United Kingdom . |
| 2180157 | 3/1987 | United Kingdom . |
| 2182244 | 5/1987 | United Kingdom . |
| 2191500 | 12/1987 | United Kingdom . |
| 2194426 | 3/1988 | United Kingdom . |
| 2200551 | 8/1988 | United Kingdom . |
| 2201593 | 9/1988 | United Kingdom . |
| 2204487 | 11/1988 | United Kingdom . |
| 2206027 | 12/1988 | United Kingdom . |

OTHER PUBLICATIONS

Chemical Abstracts 89:74468t (1978).
Chemical Abstracts 83:57001u (1975).
Chemical Abstracts 84:14958q (1976).

*Primary Examiner*—Ronald W. Griffin

[57] ABSTRACT

Devices, compositions and the like which have or contain at least one inorganic pyrophosphate salt. The devices or compositions are used to reduce or prevent tartar accumulations on dog teeth.

5 Claims, No Drawings

DEVICES, COMPOSITIONS AND THE LIKE HAVING OR CONTAINING AN INORGANIC PYROPHOSPHATE

BACKGROUND OF THE ART

1. Field Of The Invention

The invention relates to devices, compositions and the like having or containing an anti-tartar agent. The invention further relates to processes of preventing or reducing tartar formation on dogs' teeth by means of such devices, compositions and the like.

2. Background Art

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars. Mature calculus consists of an inorganic portion which is largely calcium phosphate arranged in a hydroxylapatite crystal lattice structure similar to one, enamel and dentine. An organic portion is also present and consists of desquamated epithelial cells, leukocytes, salivary desiment, food debris and various types of microorganisms. As the mature calculus develops, it becomes visibly white or yellowish in color unless stained or discolored by some extraneous agency. In addition to being unsightly and undesirable from an aesthetic standpoint, the mature calculus deposits are constant sources of irritation of the gingiva and thereby are a contributing factor to gingivitis and other diseases of the supporting structures of the teeth, the irritation decreasing the resistance of tissues to endogeneous and exogenous organisms.

A wide variety of chemical and biological agents have been suggested in the art to retard calculus formation or to remove calculus after it is formed in humans. Mechanical removal of this material is done toutinely in humans.

German Patent No. 3,426,203 discloses a chewing article for dogs consisting of 92 volume parts of raw skin, 4 volume Parts of lime and 4 volume parts of feed salts mixture containing (per 100 g) 700 mg of potassium, 1500 mg of carbonate, 1000 mg of calcium, 110 mg of phosphate, 40 mg of iron and 1 mg of iodine. The article is prepared from cow skin by stripping the skin, and subjecting the subcutaneous material to neutralization to pH 6, treating with a solution of iodine-containing feed salt and lime, shaping to form the article and drying.

U. S. Pat. No. 4,145,447 discloses a hard, unit-integral, unitized, self-contained, compact, chew-resistant nutritionally balanced animal food product 3 final having a density of at least about 0.5 oz./in$^3$, a final water content of at least about 5.5 percent by weight, and a breaking force of at least about 60 psi. The animal food contains, for example, dried meals, dried fish, dried dairy products, fish meal, fish flour, cereals, flours carbohydrates, dried fruits, etc., with or without food additives or supplements such as vitamins, minerals, medicinals, etc., for example chemicals, enzymes, etc., capable of removing plaque or tartar from the animals' teeth, etc.

U. S. Pat. No. 4,044,158 discloses the use of tetrasodium pyrophosphate as a chelating agent in semi-moist pet foods. The neutral chelating agent is used in a semi-moist pet food having a pH of from 6.3 to 7.2 and which comprises about 5 to about 50 percent by weight meat or meat by-products, about 15 to about 50 percent moisture, and about 1 percent to about 26 percent by weight vegetable protein. The vegetable protein, an amyulaceous material, and the chelating agent, it is taught, forms a composition which replaces part of the caseinate binder customarily present in a semi-moist pet food. No mention is made of any antitartar effectiveness of the pet food.

U. S. Pat. No. 4,215,149 discloses a process for maintaining the palatability of a pet food by coating particulates having a moisture content of less than 15 percent with fat and then with a monoalkali metal or monoalkaline earth metal salt of phosphoric acid to make the food more palatable to cats. Exemplary salts are monosodium phosphate and monocalcium phosphate.

U. S. Pat. No. 3,639,569 discloses the use of a tris(phosphonoalkyl)amine in a dentifrice composition with a dentifrice abrasive selected from the group consisting of beta-phase calcium pyrophosphate, particulate thermosetting polymerized resin, alumina, sodium metaphosphate, and mixture thereof, or in a mouthwash composition, or in a chewing gum composition or dental prophylaxis paste composition. The patent discloses that the use of inorganic pyrophophates as anti-calculus agents in oral compositions has the problem of hydrolysis in aqueous products and loss of activity prior to the termination of the normal shelf-life of such products. The patent also teaches that calculus inhibition by chelation of calcium ion may seriously damage tooth structure by decalcification.

U. S. Pat. No. 3,957,964 discloses microcapsules containing essential oils of mint flavor in a dentifrice adapted to release a plural flavor-burst signaling the onset of and the completion of a toothbrushing operation. The dentifrice may be a toothpaste having dicalcium phosphate as a polishing agent.

U. S. Pat. No. 3,959,458 discloses the use of from about 0.2 to about 8 percent by weight of an orally acceptable monofluorophosphate with an anticalculus agent which is a condenation product of ammonia and phosphorus pentoxide or with a polyphosphonate in an oral composition. The oral composition may further contain a calcium pyrophosphate abrasive. The patent teaches that sodium or 4 Calcium monofluorophosphate, when used in combination with the anticalculus agents, exhibit no detectable damage to silicate fillings in the mouth whereas other anticaries agents, such as sodium fluoride, do exhibit damage. It is also taught that below about pH 5.0 some of the anticalculus agents can damage dental enamel.

U. S. Pat. No. 4,314,990 discloses the use of a phosphate buffering agent, which provides phosphate ions to maintain the pH of a slurry in the range of about 6.8 to 8.0, in a toothpaste compositoin which comprises 6 to 45 percent of a silica dental abrasive, from about 0.01 to 3 percent of a fluoride ion source, from about 10 to 45 percent of water, and about 30 to 70 percent of humectant.

U. S. Pat. No. 4,323,551 discloses the use of a tetraalkali metal pyrophosphate salt to provide from about 0.5 to 5 percent of the $P_2O_7$ species in a mouthwash composition comprising 0.02 to 0.2 percent of a quaternary ammonium compound, and a carrier liquid wherein the pH is adjusted to about 7.0 to 9.5 with a mineral or organic acid.

U. S. Pat. No. 4,421,527 discloses the use of a precipitated amorphous silicon dioxide prepared by acidulation in an abrasive composition in a toothpaste that contains fluoride. Phosphoric acid is disclosed as an acidulant. Soluble phosphates, such as the pyrophosphates, are taught as improving fluoride pellicle penetration.

U. S. Pat. No. 4,515,770 discloses a process wherein a soluble source of phosphate ions or a soluble source of calcium ions is uniformally distributed through sucrose in crystalline form as a result of dissolution of the sucrose and soluble source of calcium or phosphate ions in water followed by evaporation of the water solvent. It is taught that it is of substantial importance that the calcium or phosphate ion source be as rapidly soluble in saliva as the sugar so that the protective ions will migrate to salivary retention areas as rapidly as the sugar. A material, it is taught, which is cariogenic by virtue of directly or indirectly participating in the lowering of pH in salivary retention areas is rendered non-cariogenic by treatment to incorporate enough of either a calcium or phosphate ion source to keep the acidic medium from dissolving the tooth enamel. It is also disclosed that systematically administered phosphates are said to differ in cariostatic activity depending on the type of anion (cyclictrimeta-, hexameta-, ortho-, and pyrophosphate, increasing in effectiveness in that order). It is further taught that these developments have unfortunately resulted in only minor advances in prevention of carious degradation of teeth because none of the "remineralization" processes have been shown to be consistently effective.

U. S. Pat. No. 4,515,772 discloses the use of from about 10 to about 70 percent of a dental abrasive selected from the group consisting of insoluble metaphosphates, alumina, thermosetting polymerized resins, and silica from about 50 to about 3,500 ppm of fluoride ions from a fluoride ion source, and an amount of a pyrophosphate salt selected from the group consisting of dialkali metal and mixtures of dialkali metal and tetraalkali metal pyrophosphate salts sufficient to provide at least 1.5 percent $P_2O_7$. The pyrophosphate ion is provided by a of $P_2O_7$ mixture of disodium pyrophosphate and tetrasodium pyrophosphate. The fluoride ion source is disclosed as an essential component. The upper limits on the sodium pyrophosphate salts are determined by solubility considerations, while the tetrapotassium level is established for taste reasons. It is further taught that surpisingly mixtures of certain pyrophosphate salts can provide a safe and effective anti-calculus product while also not presenting difficult formulation problems.

U. S. Pat. No. 4,532,124 discloses the use of a plaque mineralizing aqueous solution comprising urea, a fluoride salt, a water-soluble calcium salt, and a water-soluble phosphate salt in the mineralization of dental plaque. It is disclosed that high plaque calcium and inorganic phosphate levels will lower the critical pH, that is, the pH which plaque must reach before it becomes unsaturated with respect to biological apatite, and enamel dissolution commences. The urea is metabolized by bacteria to produce alkali in plaque. Aspartame and amino acids may be substituted for the urea.

U. S. Pat. No. 4,540,584 discloses the use of coral sand as an effective component in a mineral supplement in an amount sufficient to provide calcium carbonate as a mineral supplemental for humans, such coral sand also containing $PO_4$. The composition, is useful for replenishing calcium and phosphorous, as well as other minerals. Acidic foods tend to result in decayed teeth and bone fractures because of calcium poverty.

U. S. Pat. No. 3,567,459 discloses conversion of a hot melt of sugar having a moisture content less than 5 percent to a dough-like bone-forming composition by incorporation of nutritional fillers, fatty flavoring materials, and fat-absorbing farinaceous materials. The composition is formed and cooled. The patent teaches mastication of bones provides teeth cleaning benefits stemming from abrasion and other contacts of bone fragments.

U. S. Pat. No. 3,701,830 discloses the use of a neutral protease enzyme for removing plaque from and preventing the formation of calculus on the teeth of dogs wherein the neutral protease is obtained by fermentation with a strain of Bacillus suptilis or Bacillus sterothermophilus.

U. S. Pat. No. 3,882,257 discloses a process where 75 percent by weight of bones is admixed with 23.5 percent by weight of animal by-products, and the mixture is bound with salt in the preparation of a pet food having about 40 percent natural animal protein. The product enables a dog to exercise his jaws and gums to remove tartar from teeth.

U. S. Pat. No. 3,899,607 discloses a dough mixture which is worked and shaped at a temperature of 170° to 220° F to form a simulated bone having a structural matrix; or cooked, dried to a moisture content of between 5 and 12 percent by weight, ground and mixed with a dextrin adhesive to form a simulated bone having a structural matrix.

U. S. Pat. No. 4,364,925 discloses that an enzyme for removing plaque and/or tartar from the teeth is included in a chew-resistant layer of an integral chew-resistant multi-layer animal food system having a structure supporting fibers. U. S. Pat. Nos. 3,194,738 and 3,686,393 also relate to the use of enzymes for inhibiting plaque.

U. S. Pat. No. 3,488,419 discloses the use of a polyphosphonate or salt thereof in compositions like dentrifices, mouthwashes, prophylaxis pastes and topical solutions. The patent teaches that inorganic polyphosphates, such as pyrophosphates, hydrolyze in aqueous products and do not remain in active form throughout the normal shelf-life of such products. Calculus and crystal growth inhibition tests on rats using calculus prophylaxis are disclosed. The patent also teaches that calculus inhibition by chelation of calcium ion may seriously damage tooth structure by decalcification.

U. S. Pat. No. 3,535,420 discloses the use of a cyclic tetraphosphonic acid as a anti-calculus agent in an oral composition. The patent teaches that inorganic polyphosphates, such as pyrophosphates, hydrolyze in aqueous products and do not remain in active form throughout the normal shelf-life of such products. It is also taught that although certain of the art-disclosed chelators are purportedly safe for use on dental enamel, the chemical similarity of calculus to the tooth structure limits the usefulness of the chelation approach because the more effective chelators can seriously damage the tooth structure by decalcification. The cyclic tetraphosphonates are calcium sequestrants, but they retard calculus formation by a mechanism that is believed to involve the inhibition of hydroxylapatite crystal growth rather than calcium sequestering.

U. S. Pat. No. 3,686,393 discloses the use of a dextranase used to eliminate dental plaque formation.

U. S. Pat. No. 3,956,479 discloses the use of a quaternary ammonium compound having a carbamate, or a thiocarbamate, or a dithiocarbamate, or a carbamide group in an oral preparation. The compounds are effective in reducing caries and inhibiting formation of oral calculus.

U. S. Pat. No. 4,003,971 discloses the use of a dentifrice component in the production of dentifrice speckles. Antimicrobial agents for incorporation into oral dentifrice formations may be effective by reducing dental plaque or inhibiting the formation of dental calculus.

U. S. Pat. No. 4,254,101 discloses the use of from about 6 to 45 percent of a silica dental abrasive, from about 30 to 70 percent of a humectant, and from about 0.03 to 1.0 percent of a carboxyvinyl polymer in a toothpaste composition. The use of optional anticalculus agents in amount of from about 0.01 to 2.5 percent by weight of the toothpaste composition are taught.

U. S. Pat. No. 4,472,373 discloses the use of a pyridium salt as an anti-plaque agent in a flavored alcoholic carrier. Phosphates, such as calcium pyrophosphate, are disclosed as dentifrice abrasives.

U. S. Pat. No. 4,153,732 discloses the use of at least one soluble aluminum ion containing salt with adipic acid, ascorbic acid, or mixtures thereof as a cariostatic additive for comestibles. The patent teaches that calcium pyrophosphate and insolbule sodium metaphosphate abrasives coact with aluminum fluoride in dentifrice compositions.

U. S. Pat. No. 4,627,977 discloses an oral composition, such as, a toothpaste (including gel or cream), mouthwash, lozenge, chewing gum or tooth powder, containing a calculus-inhibiting amount of a linear molecularly dehydrated polyphosphate salt (e.g., a water-soluble alkali metal pyrophosphate) to inhibit enzymatic hydrolysis of said polyphosphate salt in saliva, a combination of a fluoride ion-providing source and a synthetic linear polymeric polycarboxylate. See also British Published Patent Application No. 2,180,157.

U. S. Pat. No. 4,678,662 discloses calcium carbonate particles coated with at least one pyrophosphate derivative, such as, sodium dihydrogen pyrophosphate and tetrasodium pyrophosphate.

European Published Patent Application No. 0236920 discloses a dentifrice comprising essentially insoluble calcium pyrophosphate as an abrasive and a clinically effective amount of soluble pyrophosphate, such as, tetrasodium pyrophosphate, or tripolyphosphate as an anticalculus agent.

U. S. Pat. No. 4684,518 discloses a process for reducing the incidence of calculus on dental enamel. The enamel surfaces in the mouth are contacted with a composition comprising a soluble pyrophosphate source capable of providing at least 1.5 percent of $P_2O_7$ and from about 50 to about 3500 ppm of fluorine.

U. S. Pat. No. 4,722,461 discloses an oral composition in the form of a mouthwash or liquid dentifrice comprising: an amount of a fluoride ion source sufficient to supply from about 50 ppm to about 3500 ppm of fluoride ions; an amount of a pyrophosphate salt selected from the group consisting of dialkali metal and mixtures of dialkali metal and tetra-alkali metal pyrophosphate salts sufficient to provide at least 1.5 percent of $P_2O_7$; and water. The pH of the composition is percent of $P_2O_7$ and water. The pH of the composition 1 from about 6.0 to about 10.0. Calcium pyrophosphate is termed to be an abrasive. See European Published Patent Application No. 0097476.

British Published Patent Application No. 2,201,593 discloses an oral composition in the form of a toothpaste effective in reducing calculus comprising: a safe and effective amount of a soluble pyrophosphate salt or mixture of the salts; from about 5 to about 60 percent of a suitable toothpaste abrasive; an amount of a fluoride ion source sufficient to provide from about 50 ppm to about 3500 ppm fluoride; from about 5 to about 60 percent of humectant selected from the group consisting of sorbitol, glycerine, polyethylene glycols, mineral oil, and mixtures thereof; from about 0.3 to about 5 percent of a surfactant selected from the group consisting of alkyl sulfate surfactants, ethoxylated alkyl sulfate surfactants and mixtures thereof; and water. The composition has a pH of from about 6 to about 10, is substantially free of polyethylene glycols having fewer than six ethoxy units and short chain monohydric alcohols and has potassium ions present at a level of from about 0.5 to about 7 percent. The soluble pyrophosphate salt can be, for example tetrapotassium pyrophosphate, tetrasodium pyrophosphate, sodium acid pyrophosophate and mixtures thereof.

U. S. Pat. No. 4,806,340 discloses an oral dentifrice composition such as a toothpaste, dental gel, toothpowder, dental tablet or lozenge containing as anticalculus agent about 4.3 to about 7 percent of alkali metal pyrophosphates comprising at least 4.3 percent of tetrapotassium pyrophosphate alone or admixed with up to 2.7 percent of tetrasodium pyrophosphate, and as inhibitors against enzymatic hydrolysis of such agent in saliva, a fluoride and preferably up to about 3 percent of a synthetic anionic polymeric polycarboxylate. The composition is used in a program of oral hygiene and/or for inhibiting dental calculus. It is known that saliva contains acid phosphatase, alkaline phosphatase and pyrophosphatase enzymes. It is considered that any one of the three enzymes may adversely affect pyrophosphates as an inhibitor of hydroxyapatite formation and calculus. It is accordingly apparent that an anticalculus pyrophosphate dentifrice composition, should inhibit, reduce or nullify the destructive activity of all three salivary enzymes. See also British Published Patent Application No. 2,182,244.

Australian Published Patent Application No. 168071 discloses a dialkali metal-alkaline earth metal pyrophosphate containing about 1 to about 5 percent by weight of chemically combined fluorine. The composition is a dentifrice base. The method of producing the fluorinated dialkali metal-alkaline earth metal pyrophosphate, which comprises reacting together, in the presence of an aqeuous medium, a water-soluble metal fluoride, an alkali metal pyrophosphate (such as, tetrasodium pyrophosphate), and a water soluble alkaline earth metal salt. The reactants being employed in the proportions required to yield a dialkali metal-alkaline earth metal pyrophosphate containing about 1 to about 5 percent by weight of chemically combined fluorine.

British Patent No. 777,556 discloses a dentifrice composition which contains a fluoride compound which releases fluoride ions in water, a calcium polyphosphate polishing agent, and a calcium ion suppression agent to maintain the effect of the fluoride upon ageing.

U. S. Pat. No. 4,822,626 discloses a process of producing a biscuit with a baked-on proteinaceous coating. The process includes preparing a dough piece from a dough comprising flour, meal, fat and water; and enrobing the dough piece with a viscous coating formation comprising 10 to 30 weight percent of a dextrin carrier, 10 to 50 weight percent of meat, 10 to 30 weight percent of a glazing agent, 1 to 5 weight percent of polysaccharide gum, 5 to 15 weight percent of a monosaccharide sugar, 5 to 15 weight percent of a disaccharide sugar, and water, all based upon the total dry solids. The dough piece is baked to form a dry biscuit with a baked-on coating. The glazing agent can comprise a gelatin or a modified food starch, and the polysaccharide gum can be a xanthan gum. Biscuits produced by the process and a bakable proteinaceous coating formulation as employed in step (b) are disclosed.

BROAD DESCRIPTION OF THE INVENTION

An object of the invention is to provide devices, compositions and the like containing pyrophosphate. A further object of the invention is to provide processes for the prevention or reduction of tartar accumulation on the teeth of dogs by such devices, compositions and the like. Other objects and advantages of the invention are set out herein or are obvious herefrom to one skilled in the art.

The objects and advantages of the invention are achieved by the compositions and processes of the invention.

Tartar is an incrustation of the teeth consisting of salivary secretion, food residue and various salts, such as, calcium carbonate or phosphate. Tartar is also termed dental calculus.

Caries are cavities or decay of the teeth which begins at the surface of the tooth and may progress through the dentine into the pulp cavity. It is believed that the action of microorganisms in the mouth on ingested sugars and carbohydrates produces acids that eat away the enamel. By preventing the formation of calculus or tartar, the invention formulation is in effect an anti-cariogenic agent.

The invention involves an animal or dog food, such as, a dog biscuit, having a soft, edible center which contains at least one inorganic pyrophosphate. The center is made soft by the inclusion of a softening agent, such as, at least one humectant. The preferred humectant is propylene glycol. The animal food reduces or prevents the accumulation of tartar on the animal's teeth.

The invention also involves animal foods, such as, dog foods, having a coating containing at least an inorganic pyrophosphate. The coated animal food reduces or prevents the accumulation of tartar on the animal's teeth.

The invention also involves swabs, gauze and other like materials having absorbed/adsorbed therein and/or thereon a solution containing at least one inorganic pyrophosphate. The treated swab or treated gauze reduces or prevents the accumulation of tartar on the animal's teeth.

The invention further involves swabs, gauze or other like materials having thereon and/or therein a coating containing at least one inorganic pyrophosphate. The coated swab or coated gauze reduces or prevents the accumulation of tartar on the animal's teeth.

The invention involves meat jerky, such as, beef jerky, having absorbed/adsorbed therein and/or thereon a solution containing at least one inorganic pyrophosphate. The treated meat jerky reduces or prevents the accumulation of tartar on the animal's teeth.

The invention involves meat jerky, such as, beef jerky, having a coating therein and/or thereon a coating containing at least one inorganic pyrophosphate. The treated meat jerky reduces or prevents or reduces the accumulation of tartar on the animal's teeth.

The invention still further involves a process of preventing or reducing tartar accumulation on the teeth of an animal, comprising:
  (a) spraying an aqueous solution containing at least one inorganic pyrophosphate onto an animal food; and
  (b) having an animal consume the treated animal food.

The invention deals primarily with dogs, but has a scope of teeth bearing non-human mammals and other animals, such as, cats and dogs.

DETAILED DESCRIPTION OF THE INVENTION

As used herein, all parts, percentages, ratios and proportions are on a weight basis unless otherwise stated herein or otherwise obvious herefrom to one skilled in the art. As used herein, all temperatures are in degrees Fahrenheit unless otherwise stated herein or otherwise obvious herefrom to one skilled in the art.

The invention involves a dog food, such as, dog biscuits, having a soft center containing at least one inorganic pyrophosphate. The center is softer than the rest of the dog biscuit, which can be a soft or hard dog biscuit. The center is made soft by the inclusion of at least one softening agent, such as, at least one humectant.

The outer portion of the dog food, such as, dog biscuits, can be made from any suitable dog food dough, such as, suitable dog biscuit dough. Any suitable dough comprising at least one flour, meal, fat and water can be employed for the product. For instance, when the desired product is a canine biscuit, a conventional dough for dog biscuits can be used, optionally containing discrete particles of meat and/or meat byproducts or farinaceous material. Such doughs typically contain fat solids. Examples of suitable doughs for the production of hard dog biscuits are disclosed in U. S. Pat. No. 4,454,163, and suitable doughs for the production of soft dog biscuits (containing humectant to control water activity) are disclosed in U. S. Pat. No. 4,454,164. The pertinent portions of U. S. Pat. Nos. 4,454,163 and 4,454,164 are incorporated herein by reference. Particulate proteinaceous particles, such as particles of meat, texturized vegetable protein and/or meat byproducts can be incorporated to add flavor to the biscuits and texturize the surface. Particulate farinaceous materials such as bran particles can also be employed to texturize the interior and/or surface of the biscuits and to provide other useful properties to the product. A dough found to produce biscuits highly palatable to dogs includes suitable proportions of wheat flour, wheat meal, soybean meal, meat and bone meal, animal fat and natural flavors in admixture with water. The meal used in the doughs suitable for production of biscuits useful in the invention can comprise meat and/or bone and/or vegetable matter including farinaceous materials, materials prepared from legumes such as beans and peas, tuberous materials such as potato meal, and the like. The means can be finely or coarsely ground as desired for the texture. Flours made from any suitable farinaceous material can be used.

The doughs generally have a water activity of about 0.90 and above upon completion of mixing of the dough ingredients. A suitable dough contains farinaceous material, an edible oil, an antioxidant, an antimycotic, salt, animal fat, added vitamins and minerals, such as those disclosed in U.S. Pat. No. 4,229,485, column 5, lines 7 to 57, which is incorporated herein by reference. The compositions of the invention also preferably contain at least one animal-derived proteinaceous meal such as meat meal, bone meal and fish meal. A good biscuit dough for producing the biscuits of the invention contains about 50 to 60 percent by weight wheat flour, about 5 to 10 percent by weight soybean meal, about 3 to 10 percent by weight meat and bone meal, about 1 to 5 percent wheat meal, about 1 to 5 percent animal fat preserved with BHA, about 20 to 30 percent by weight water, and about 2 to 5 percent by weight of natural flavors, vitamin and mineral preblend, and acidulant.

The soft center portion of the dog biscuit contains a softening agent if it is made from a dog biscuit dough. Any suitable softening agent can be used. The preferred humectant is propylene glycol. Examples of other suitable humectants are corn syrup, sugar and polyalcohols, such as, sorbitol and glycerin. Any suitable humectant known in the art can be used.

If the softening agent is used in the outer portion of the dog biscuit, more of a softening agent should be used in the central portion to make it softer than the outer portion.

The solvent used in preparing the dog biscuit dough for the center portion is most preferably water, but other non-toxic, edible solvents, such as, ethanol or ethanol/water, can be used. The problem of the necessity of solvent removal from the dough due to toxicity is to be avoided. If a mixture of ethanol and water is used, the amount of ethanol in the mixture is generally about 5 to 60 percent, preferably about 5 to about 25 percent. When one or more of the inorganic pyrophosphates is not water soluble, it may be ethanol soluble. It may be necessary to use a non-aqueous solvent, or mixture of water therewith, to incorporate the inorganic pyrophosphate.

The invention includes the use of at least one inorganic pyrophosphate. Preferably the inorganic pyrophosphate(s) is water soluble. A mixture of pyrophosphates can be used to provide a desired pH. Water-insoluble or difficulty soluble inorganic pyrophosphates can be used.

The pH of the dough can be adjusted using an inorganic base (e.g., KOH, NaOH, CaOH, LiOH, MgOH, etc.) or an inorganic base (e.g., $H_2SO_4$, HCl, etc.), but this approach has the disadvantages of possibly causing a misbalance or overabundance of one or more chemical entities and possibly introducing unwanted salts.

Generally 0.1 to 10 weight percent, preferably about 0.5 to about 3.5 weight percent and most preferably about 1.4 to about 2.5 weight percent of inorganic pyrophosphate is used.

When a mixture of tetrasodium pyrophosphate (TSPP) and sodium acid pyrophosphate in aqueous solution at the 5 weight percent level was incorporated in dog biscuit dough, there was reduced dough gluten development, the dog biscuits were bleached (whitish) and crumbly, and the dog biscuits were softer (a hardness problem) than the control dog biscuits. At the level of 3 weight percent of a mixture of tetrasodium pyrophosphate and sodium acid pyrophosphate, the same problems occurred, but less severely. The addition of the inorganic pyrophosphates in dry from to the dry ingredients in the dough preparation basically eliminated the above problems. It was also found that better results were secured by using the inorganic phosphates in powder form as opposed to granular form.

The inorganic pyrophosphates are preferably alkali metal pyrophosphates. The preferred alkali metal pyrophosphates are tetrasodium pyrophosphate and tetrapotassium pyrophosphate. An example of a useful tetraalkali metal pyrophosphate is tetralithium pyrophosphate. Alkaline earth metal pyrophosphates are also useful, but they are generally insoluble in water. Preferably, the inorganic pyrophosphates are soluble in water.

Examples of dialkaline metal pyrophosphates are dicalcium pyrophosphate, dibarium pyrophosphate and dimagnesium pyrophosphate. Trialkali metal monoacid pyrophosphates, such as, trisodium hydrogen pyrophosphate, can be used. Monoalkali metal triacid pyrophosphates, such as, disodium trihydrogen pyrophosphate, can also be present in limited amounts. Examples of other inorganic pyrophosphates include manganese pyrophosphate and dizinc pyrophosphate.

Tetrasodium pyrophosphate, one part, is soluble in 13 parts of cold water and in 2.5 parts of boiling water. It is insoluble in ethanol. Dicalcium pyrophosphate is practically insoluble in water. The invention use of the term "solution" includes slurries, suspensions and the like. Tetrapotassium pyrophosphate is freely soluble in water and is insoluble in ethanol.

Most preferably a mixture of sodium acid pyrophosphate and tetrapotassium pyrophosphate is used (in a ratio to achieve the desired pH).

The maximum allowable GRAS level in a composition for sodium acid pyrophosphate (SAPP) is 2.1 weight percent and tetrapotassium pyrophosphate (TKPP) is 1.4 weight percent in baked goods. If GRAS levels change (rise) or if higher levels are allowed by the regulatory agencies, higher levels can be used in the invention. TKPP delivers approximately 52.65 percent of $P_2O_7$; SAPP delivers about 78.36 percent of $P_2O_7$; and TSPP delivers about 65.4 percent of $P_2O_7$.

The most preferred invention dough contains trisodium monoacid pyrophosphate (that is, sodium acid pyrophosphate or SAPP) and tetrapotassium pyrophosphate in a weight ratio of about 60 to 40.

The pyrophosphate(s) is used in sufficient amount to deliver generally from about 0.1 to about 5, preferably from about 0.5 to about 3.5, most preferably 1.4 to 2.5 weight percent (based on the total composition), of $P_2O_7$.

A study of the application of aqueous solutions of a mixture of tetrasodium pyrophosphate and sodium acid pyrophosphate to the teeth of dogs by spraying for one month resulted in dose response data. The aqueous solutions containing 5 and 3 weight percent of a mixture tetrasodium pyrophosphate and sodium acid pyrophosphate resulted in significant reductions in tartar accumulation. The aqueous solutions containing 1.5 and 0.5 weight percent of a mixture of sodium acid pyrophosphate and tetrasodium pyrophosphate resulted in directional trends of reductions in tartar accumulation. See also U.S. Pat. No. 3,323,551.

The ratio of sodium acid pyrophosphate (SAPP) to tetrapotassium pyrophosphate (TKPP) is generally between 4 to 1 and 3 to 7, preferably between 7 to 3 and 1 to 1, most preferably about 3 to about 2. SAPP has a pH of 4.2 and TKPP (and TSPP) has a pH of 10.2, so the combination of SAPP and TKPP (or TSPP) provides a resultant pH which is a balance of the pHs of the two components.

The pH of the dough of the inner portion containing at least one inorganic pyrophosphate compound (salt) is generally in the range of about 4 to about 10.5, typically from about 4.5 to about 7.5, preferably from about 5 to about 7, most preferably between about 5.6 and about 6.1. Milk Bone ® dog biscuit has a pH of 6.1 to 6.4. Tartar reduction is indicated to be best at a neutral pH and palatability is indicated to be best at a slightly acidic pH, so the best mode contemplates a balance of such two factors in any commercial product.

The dough ingredients are generally mixed at a temperature of about 45° to about 140° F., preferably about 60° to about 125° F.

The dog biscuit dough for the outer portion and the inner portion can be mixed using any suitable or conventional equipment. For example, the mixing can be at 20 to 100 rpm. For example, a dry blending step (dries and the inorganic pyrophosphates) can be done typically at room temperature for a period of time of about 3 minutes to about 20 minutes. The dry-blended mixture can then be mixed with the hot water to form a first stage dough. The water which can be admixed with the dry-blended mixture is typically at a temperature of about 65° to about 150° F. The hot water can be added, with mixing, over a period of time of about 3 minutes to about 6 minutes to form the first stage dough. Then, the fat portion of the biscuit dough can be admixed with the first stage dough to form the final stage dough. The fat portion can be added at a temperature at which it is at least fluid, typically at about 100° to about 150° F. The fat portion can be mixed for a period of time which is sufficient to form a dough whose homogeneity is visually apparent. A typically final mixing time is about 3 to about 5 minutes.

If there are machinability and dough structure property problems with the center portion dough, the addition of water should solve such problems. If the use of the higher water levels caused the dough to be so sticky as to cause problems in a sigma or rotary mixer (but normally not a significant problem in a continuous mixer). The addition of more tallow to the dog biscuit dough should assist in more effective mixing and help to keep the dough from being so sticky that it clings to a rotary molder. Preferably the tallow level is about 2.6 to about 3.1 weight percent (most preferably about 2.85 weight percent), as opposed to a tallow level of about 2.46 weight percent in Milk Bone ® dog biscuits. Also, the tallow provides a taste which dogs like.

Formation of the dough is achieved at about atmospheric pressure with mixing of the components being conveniently achieved in an upright sigma blade mixer or other bakery-type mixers. The various ingredients can be added over a period of time or in a one-shot manner according to the above order of addition. However, melted fat and water can be added simultaneously and mixed for 6 to 10 minutes.

The center portion of the dog biscuit can also be a fruit filler, e.g., a fruit gel composition, containing at least one inorganic pyrophosphate.

The dog food composition, such as, dog biscuits, having a soft center portion can be prepared by any suitable method, such as, convention deposition of the center portion on a dough piece and then capped by another dough piece, the edges of such pieces preferably being pressed together. Such dough pieces can be formed in any suitable or conventional manner, such as, by extrusion, stamping, cutting or molding. Preferably the food composition is prepared by the coextrusion of the outer portion and the soft center portion. Any suitable dog food composition shapes or dog biscuit shapes can be used, such as, bone-shaped canine biscuits. Holes can be formed in the dog food composition or dog biscuits to facilitate the escape of moisture during baking, cooking and/or drying.

The dog biscuit dough pieces can be baked using any suitable or conventional equipment and conditions. For example, the dog biscuit dough pieces can be passed into an oven such as a conventional band oven where the biscuits are baked. The conveyor belts of the oven can be coated with an edible lubricant such as a natural or synthetic cooking oil or shortening to facilitate separation from the conveyor belts of the baked products. Temperatures in the range of about 300° to about 600° F. can be used. The baked dog biscuits can also be subjected to subsequent drying at temperatures of about 200 to 400° F., either within the baking oven or separately, to produce the desired moisture content in the final product.

The formed dog biscuit dough pieces are baked, followed by drying, to achieve a shelf stable product without the need of any moisture barrier protection. Baking and drying temperatures and times are those conventionally used in the production of a dry canine biscuit. The pieces are dried to obtain a biscuit having a water activity of 0.70 or less. Typically, baking temperatures and times are about 300° F. to about an average of 475° for about 25 minutes to about 8 minutes. Drying conditions are typically about 200° to about 325° F. for about 25 minutes to about 12 minutes in a forced air dryer. On a weight basis, the moisture content of the final biscuit product is less than or equal to about 15 percent by weight and preferably about 10 to 12 percent by weight of the final biscuit at 70 percent relative humidity The invention product does not include any fluorine-containing compound or other fluoride ion source, or quaternary ammonium compounds. Also the invention product does not include any organic pyrophosphates.

The invention deals primarily with dogs, but has a scope of teeth-bearing non-human mammals, such as, cats.

The invention composition can be used to reduce and control tartar accumulation on canine teeth. Based upon the weight of commercial Milk Bone ® dog biscuits: 12 small invention dog biscuits per day, 10 medium invention dog biscuits per day, 6 large invention dog biscuits per day or 4 extra large invention dog biscuits per day will supply about ¼ to ⅓ of a dog's caloric requirement.

The invention also involves animal foods, such as, dog foods, having a coating containing at least one inorganic pyrophosphate. The above information regarding inorganic pyrophosphates also applies here; the coating can contain the same amounts and type of. inorganic pyrophosphates as in the case of the soft center portion.

The coating is preferably applied to the animal food in the form of a liquefied coating formulation by any suitable means, such as, dipping, spraying, etc. The coating can encompass all or part of the animal food.

The liquefied coating formulation best contains at least one suspension agent. The preferred suspension agent is a polysaccharide gum, most preferably xanthan gum. Preferably about 0.05 to 1.75 weight percent of polysaccharide gum (xanthan gum) is used. Xanthan gum is one of the few gums which acts as an acceptable suspension agent in the invention. The xanthan gum is an excellent agent for controlling the bodying effect, as it is stable over a broad temperature range, i.e., it holds the same viscosity over a large temperature range without any separation of the coating ingredients. The xanthan gum has a bodying effect so that little or no separation occurs. Other suitable gums and mucilages can be used.

Malto-dextrin produced by hydrolyzing corn starch is preferred; it serves as a carrier (bodying), binding agent and suspension agent and helps the appearance of the coating; and it is a preferred ingredient. Other malto-dextrins can also be used for the same functions.

An adhesive or binding agent, such as, malto-dextrins, is needed in the coating slurry to help the coating material bind (adhere) to the raw hide when the raw hide is dipped in the coating slurry. Preferably about 5 to about 15 weight percent of the malto-dextrin is included in the coating material.

A carrier, such as, starch or a modified food starch, is included in the coating formulation. Preferably about 0.1 to about 5 weight percent of the food starch or modified food starch is included in the coating material. The food starch or modified food starch also serves to control the viscosity.

Animal fat preferably is included for flavor purposes. Other suitable flavorants can be used or included, particularly salt. The flavorants can be any dairy product flavorant, such as milk or cheese, meat flavorants, such as, liver or beef, poultry and fish. Flavorants help provide palatability for the invention coating.

Preferably a hydrogenated vegetable oil is included in the coating formulation for sheen and to modify the melting point of the formula fats in the finished product. It also helps to prevent flaking of the coating; also the coating does not have a tacky feeling.

Any suitable colorant can be included in the coating formulation. The preferred colorant is caramel color which also provides some flavor to the product.

The coating also incorporates sufficient water to achieve the liquefied coating composition. Amounts of the other ingredients are those which are effective to achieve their functions in the coating formulation.

The preferred coating formulation, besides the inorganic pyrophosphates, contain animal fat, a surfactant, such as, a modified lethicin, polysaccharide gum, a modified food starch, flavorant, colorant, hydrogenated vegetable oil, a carrier, such as a malto-dextrin, and water. A suitable humectant, preferably propylene glycol, can be used in the coating formulation.

The coating formulation should be viscous enough so that the coating formulation generally only coats the surface regions of the animal food. The presence of coating in the surface regions of the animal food helps to anchor the resultant coating and to prevent the coating from easily being separated from the animal food during handling and shipping. Basically though the coating is strictly a surface phenomena on the animal food.

The coating slurry can be applied to the animal food by any suitable means, such as, spraying, dipping, soaking in a container, etc. The coating slurry is applied generally at a temperature of 45° to 200° F., preferably at about 60° to about 190° F., and most preferably at about 180° F. The coating slurry has a low microbial profile at such higher temperatures.

After treating the raw hide with the pyrophosphate slurry, the coated animal food is dried and/or baked. While the coated animal food is preferably air dried, it is also advantageous to dry the coated animal food using applied heat, e.g., in a hot air oven (at a temperature of say 75° F to 300° F.).

The preferred embodiment and ranges of the above type of coating is:

| Ingredients | Percentages | |
|---|---|---|
| | Specific | Ranges |
| Sodium acid pyrophosphate (SAPP), anhydrous powder, (non-leavening type) | 1.73 | 0.25–5 |
| Tetrapotassium pyrophosphate (TKPP), anhydrous powder | 1.15 | 0.25–5 |
| Salt | 0.50 | 0.05–2.50 |
| Malto-dextrin | 9.17 | 2–30 |
| Food starch modified | 2.00 | 0.1–10 |
| Colorant | 0.50 | 0.01–3 |
| Flavorant | 2.00 | 0.01–5 |
| Xanthan | 0.20 | 0.05–1.5 |
| Lecithin or modified lecithin | 1.25 | 0.5–1.75 |
| Vegetable Fat | 0.50 | 0.1–3 |
| Animal Fat | 1.00 | 0.1–5 |
| Subtotal | 20.00 | |
| Water | 80.00 | 50–about 97 |
| Total | 100.00 | |

The following coating-baking procedure is particularly advantageous:
 (a) dry blending the dry powder.
 (b) adding ¼ of the water and slurring the composition.
 (c) adding remaining ¾ of the water and mixing to form the coating formulation.
 (d) heating the coating formulation to 185° to 200° F. with intermittent stirring (add animal fat at about 125° F. during the heating).
 (e) maintaining the coating formulation at 160° to 190° F.
 (f) apply the coating material to the unbaked dough pieces.
 (g) baking the coated, unbaked dough pieces at 325° F. for 25 minutes.
 (h) drying the baked, coated dough pieces for 25 minutes at 225° F. in a forced-air dryer.

The animal food within the scope of this invention needs to have a sufficient integrity to not fall apart during processing and handling, especially, so that the coating can be applied, dried/baked, etc., without losing its integrity or cracking. The animal food is best in the form of pieces or the like, such as, kibbles, biscuits, snacks, etc. The animal food pieces can be made by any suitable forming means, such as, extruding, molding, stamping, etc. The invention composition is used to reduce and control tartar accumulation on canine teeth.

The coating containing at least one inorganic pyrophosphate salt can be applied to animal foods having soft centers which may or may not contain at least one inorganic pyrophosphate. The total amount of inorganic pyrophosphate can be distributed between the coating and the soft center.

The coating can also be composed of SEALGUM and at least one inorganic pyrophosphate. SEALGUM is a tradename of Colloides Naturels Inc. of Bridgewater, New Jersey 08807 for a coating material which provides a gummed, shiny coating. The coating, for example, can be applied in the form of a solution, slurry or emulsion by using a rotative coating machine or using spray nozzles.

The animal food can be the dog food disclosed in commonly-owned, copending U.S. application Ser. No. 242,292, filed on Sept. 9, 1988, entitled "Chewy Dog Snacks", the pertinent parts of which are incorporated herein by reference. A chewy, semi-plastic, non-extruded, non-porous, microbiologically-stable dog food which includes: 12 to about 30 weight percent, based upon the total weight of the dog food, of gelatin; at least one acidulant; at least one cereal starch-containing textural agent; at least one release agent; at least one taste agent; at least one sugar; salt; and added water. The dog food is in a molded form. The dog food has a pH of about 3 to 5, and has a moisture content of about 10 to 25 weight percent, based upon the weight of the dog food. The process for preparing the dog food includes (a) mixing the dry components and liquid components with low speed agitation and continuing the mixing until a dough is obtained; (b) forming the dough by molding or rotary molding into molded snacks or biscuits; (c) conditioning the molded dough at 185° to 200° F. for about 7 to 8 minutes; and (d) packaging the molded dog snacks or biscuits in a protective package.

The coating and dog biscuits can be those of U.S. Pat. No. 4,822,626, and copending commonly-owned U.S. application Ser. No. 304,625, filed on Feb. 3, 1989, the pertinent parts of each are incorporated herein by reference. The biscuits with a baked-on proteinaceous coating, are produced comprising steps of:
(a) preparing a dough piece from a dough comprising flour, meal, fat and water;
(b) enrobing the dough piece with a viscous coating formulation comprising 10 to 30 weight percent of a dextrin carrier, 10 to 50 weight percent of meat, 10 to 30 weight percent of a glazing agent, 1 to 5 weight percent of polysaccharide gum, 5 to 15 weight percent of monosaccharide sugar, 5 to 15 weight percent of a disaccharide sugar, and water, all based upon total dry solids; and
(c) baking the dough piece to form a dry biscuit with a baked-on coating. The glazing agent can comprise a gelatin or a modified food starch, and the polysaccharide gum can be a xanthan gum.

The coatings are modified by the inclusion of at least one inorganic pyrophosphate.

The invention also involves swab, gauze and other like materials having adsorbed/adsorbed thereon a (aqueous) solution containing at least one inorganic pyrophosphate. The above information regarding amounts, types, preferred, etc., of the inorganic pyrophosphates also apply here. The disclosure herein concerning pyrophosphate solutions (aqueous, water/ethanol, ethanol, etc.) is applicable here. The solution preferably contains a thickener, preferably a humectant, such as, corn syrup, sugar and polyalcohols, such as, propylene glycol (preferred), sorbitol and glycerin.

Swabs are small sticks having a wad of an absorbent material, preferably cotton, usually wound around one end thereof. Gauze is a loosely woven cotton (or other suitable absorbent material) surgical dressing. The gauze can have a water-proof backing.

The solution (preferably aqueous) containing can be applied to the swab, gauze and like materials by any suitable means. Preferably the sorbent or tip portion of the swabs containing the cotton or like material is dipped into the solution which is usually heated at 45° to 200° F., preferably at about 60° to about 190° F., and most preferably at about 180° F. The treated swab can be packaged in a liquid-tight container without drying. The treated swab can also be dried, preferably in a forced-air oven at a temperature of 75° to 300° F. The gauze is preferably dipped in the solution or sprayed with the solution. The solutions are usually and preferably heated as above. The treated gauze can be packaged in a liquid-tight container or package without drying. The treated gauze can also be dried as above.

The undried or dried swabs, gauze or like material are package, individually or in plurality, in liquid-tight or air-tight containers.

The undried or dried swabs, gauze or like material can be used to control or reduce tartar accumulation on animal teeth, such as, dog teeth, by contacting such teeth on a periodic basis (preferably each day) with such dried, coated swabs, gauze or like material.

The invention further involves swabs, gauze and other like materials having thereon and/or therein a coating containing at least one inorganic pyrophosphate. The above information regarding amounts, types, preferred, etc., inorganic pyrophosphates also applies here. The coating can contain the same amounts and type of inorganic pyrophosphates as in the case of the soft center portion.

The coating preferably is the coating described above which contains a surfactant, such as, lecithin or modified lecithin, xanthan gum (or other suitable polysaccharide gum), a starch or modified food starch, hydrogenated vegetable oil and a carrier, such as, malto-dextrin, flavorant (optional) and colorant (optional), but not including the animal fat. The above disclosure regarding such coating also applies to this invention embodiment, as appropriate. A suitable humectant, preferably propylene glycol, can be used in the coating formulation.

The coating can be applied to the swab, gauze and like materials by any suitable means. Preferably the sorbent or tip portion of the swabs containing the cotton or like material is dipped into the liquefied coating composition, which is usually heated at 45° to 200° F., preferably at about 60° to about 190° F., and most preferably at about 180° F. The coating can then be dried, preferably in a forced-air oven at a temperature of 75° to 300° F. The gauze is preferably dipped in the liquefied coating composition or sprayed with the liquefied coating composition. The liquefied coating compositions are usually and preferably heated as above and the drying is preferably done as above.

The dried, coated swabs, gauze or like material are package, individually or in plurality, in air-tight containers.

The dried, coated swabs, gauze or like material can be used to control or reduce tartar accumulation on animal teeth, such as, dog teeth, by contacting such teeth on a periodic basis (preferably each day) with such dried, coated swabs, gauze or like material.

The invention involves meat jerky, such as, beef jerky, having adsorbed/adsorbed therein and/or thereon a (dried or undried) solution containing a (aqueous) solution containing at least one inorganic pyrophosphate. The above information regarding amounts, types, preferred, etc., of the inorganic pyrophosphates also applies here. The solution should use an aqueous, water/ethanol or ethanol solvent. As used in this entire document, a solution can include a slurry, suspension or the like where appropriate, for example, if a water-insoluble pyrophosphate is used.

The solution can be applied to the meat jerky by any suitable means. The meat jerky, particularly beef jerky, is somewhat porous in structure. The solution is preferably applied by dipping the meat jerky in the solution, which is usually at 45° to 200° F., preferably at about 60° to about 190° F. and most preferably at about 180° F., or by spraying the solution onto the meat jerky (the solution temperatures being the same as above). The treated meat jerky can be dried by any suitable means, preferably in a forced-air oven at a temperature of 75° to 300° F.

The meat jerky can be packaged in air-tight containers.

Any meat jerky can be used. Naturally prepared jerky, also known as charqui, typically made with strips of striate muscle meat. Beef jerky products for canine consumption are usually prepared by the loaf extrusion method, the single strip extrusion method and the ribbon strip extrusion method. Coextensively aligned jerky are described in copending, commonly-owned U.S. application Ser. No. 164,418, filed on Mar. 4, 1988, and U.S. application Ser. No. 024,709, filed on Mar. 10, 1987, the pertinent portions of which are incorporated herein by reference.

The meat jerky can be used to prevent or reduce tartar accumulation on animal teeth, such as, dog teeth, by having the animal consume the treated meat jerky on a periodical (e.g., daily) basis.

The invention involves meat jerky, such as, beef jerky, having thereon and/or therein a coating containing at least one inorganic pyrophosphate. The above information regarding the amounts, types, preferred, etc., of inorganic pyrophosphates applies here.

The coating preferably is the coating described above which contains a surfactant, such as, lecithin or modified lecithin, xanthan gum (or other suitable polysaccharide gum), a starch or modified food starch, hydrogenated vegetable oil, a carrier, such as, malto-dextrin, animal fat, flavorant, colorant and water. The above disclosure regarding such coating also applied to this invention embodiment, as appropriate. A suitable humectant, preferably propylene glycol, can be used in the coating formulation.

The coating can be applied to the meat jerky gauze and like materials by any suitable means. Preferably the meat jerky is dipped into or sprayed with the liquefied coating composition, which is usually heated at 45° to 200° F., preferably at about 60° to about 190° F., and most preferably at about 180° F. The coating can then be dried, preferably in a forced-air oven at a temperature of 75° to 300° F.

The dried, coated meat jerky is packaged in air-tight containers.

The dried, coated, meat jerky can be used to reduce or reduce tartar accumulation on animal teeth, such as, dog teeth, by having the animal consume the treated meat jerky on a periodical (e.g., daily) basis.

The invention also includes the application of a solution containing at least one inorganic pyrophosphate onto an animal food, such as, dog biscuits, semi-moist dog food, kibbles, extruded dog snacks and food, coated dog biscuits, etc. The above information regarding amounts, types, etc., of the inorganic pyrophosphate also applies here. Preferably the edible solvent used in the solution is water.

The solution is preferably applied to the animal food by means of a spray device, e.g., a spray bottle or a spray can. The treated animal food is used to reduce or prevent tartar accumulation on the animal's teeth, for example, dog teeth or cat teeth, by having the animal consume such treated animal food on a periodic (e.g., daily) basis.

DEFINITIONS

SAPP is sodium acid pyrophosphate.
TSPP is tetrasodium pyrophosphate.
TKPP is tetrapotassium pyrophosphate.

What is claimed is:

1. Baked dog food comprising a soft center portion and an outer portion, the center portion comprising at least one alkali metal inorganic pyrophosphate, the center portion being softer than the outer portion, the center portion containing about 0.1 to about 10 weight percent of said at least one alkali metal inorganic pyrophosphate, based upon the total weight of the baked dog food, said at least on alkali metal inorganic pyrophosphate being water soluble, the baked dog food being slightly acidic to neutral, the baked dog food having a water activity of 0.70 or less, and the baked dog food containing 15 weight percent or less, based upon the total weight of the baked dog food, of water.

2. The baked dog food as claimed in claim 1 wherein said at least one alkali metal inorganic pyrophosphate is a combination of trisodium monoacid pyrophosphate and tetrapotassium pyrophosphate, the soft center portion is composed of a soft dog biscuit dough and said at least one alkali metal inorganic pyrophosphate, and the soft dog biscuit dough contains a humectant.

3. The baked dog food as claimed in claim 1 wherein said at least one alkali metal inorganic pyrophosphate is a combination of sodium monoacid pyrophosphate and tetrapotassium pyrophosphate.

4. Meat jerky comprising meat jerky containing at least one alkali metal inorganic pyrophosphate, the amount of said at least one alkali metal inorganic pyrophosphate being sufficient to deliver from about 0.1 to about 5 weight percent, based on the total weight of the meat jerky containing at least one alkali metal inorganic pyrophosphate, of $P_2O_7$, said at least one alkali metal inorganic pyrophosphate being water soluble, and said meat jerky being slightly acidic to neutral.

5. The meat jerky as claimed in claim 4 wherein said at least one alkali metal inorganic pyrophosphate is a combination of trisodium monoacid pyrophosphate and tetrapotassium pyrophosphate.

* * * * *